(12) United States Patent
Koolwal et al.

(10) Patent No.: US 8,270,694 B2
(45) Date of Patent: Sep. 18, 2012

(54) SYSTEMS, METHODS AND DEVICES FOR CORRELATING REFERENCE LOCATIONS USING IMAGE DATA

(76) Inventors: Aditya Koolwal, San Francisco, CA (US); Christopher R. Carlson, Menlo Park, CA (US); Federico Barbagli, San Francisco, CA (US)

( * ) Notice: Subject to any disclaimer, the term of this patent is extended or adjusted under 35 U.S.C. 154(b) by 583 days.

(21) Appl. No.: 12/428,997

(22) Filed: Apr. 23, 2009

(65) Prior Publication Data

US 2009/0268955 A1 Oct. 29, 2009

Related U.S. Application Data

(60) Provisional application No. 61/125,309, filed on Apr. 23, 2008.

(51) Int. Cl.
*G06K 9/60* (2006.01)
(52) U.S. Cl. ............................ 382/128; 706/52; 600/463
(58) Field of Classification Search .................. 382/128; 706/52; 600/463
See application file for complete search history.

(56) References Cited

U.S. PATENT DOCUMENTS 6,450,978 B1 * 9/2002 Brosseau et al. ............. 600/595
2005/0113643 A1 * 5/2005 Hale et al. ..................... 600/118

OTHER PUBLICATIONS

Shahidi et al. "Implementation, Calibration and Accuracy Testing of an Image-Enhanced Endoscopy System." IEEE Transactions on Med Imag, vol. 21, No. 12, Dec. 2002, pp. 1524-1535.*
Villard et al. "Radiofrequency ablation of hepatic tumors: simulation, planning, and contribution of virtual reality and haptics." Comput Methods Biomech Biomed Engin, Aug. 2005; 8(4) pp. 215-227.*
Thrun, S. "Probabilistic algorithms in robotics." Al Magazine 21(4), pp. 93-109 (2000).
Pluim, J.P. et al. "Mutual Information Based Registration of Medical Images: A Survey." IEEE Trans on Medical Imaging, vol. X, No. Y, 2003.
Rui, Y. et al. "Better proposal distributions: object tracking using unscented particle filter." In Proceedings of the IEEE Computer Society Conference on Computer Vision and Pattern Recognition, vol. 2, pp. 786-793 (2001).
Koolwal, A.B. et al. "An incremental method for registering electroanatomic mapping data to surface mesh models of the left atrium." Med Image Comput Comput Assist Interv. 11(Pt 2): pp. 847-854 (2008). Filed in underlying U.S. Appl. No. 61/125,309.
Baker, J.E. "Reducing bias and inefficiency in the selection algorithm." In Proceedings of the Second international Conference on Genetic Algorithms and their Application, Int'l Conference Book Coversheet, Abstract and p. 14 (1987).

* cited by examiner

*Primary Examiner* — Wensing Kuo
(74) *Attorney, Agent, or Firm* — Crawford Maunu PLLC

(57) ABSTRACT

A variety of embodiments relate to systems, methods, circuits and devices are implemented to perform location-based correlations. One such embodiment relates to a circuit-implemented method for use with an actual probe within an anatomical structure. For a virtual probe at a virtual location within a model of the anatomical structure, virtual image data captured by the virtual probe is generated. The virtual image data is assessed through a probabilistic comparison of the virtual image data to actual image data captured by the actual probe at an actual location. Based upon the assessment, a correlation is updated between the actual location of the actual probe and a sensed location of the actual probe to provide synchronicity between the sensed location and actual location. For maintaining the synchronicity between a subsequently sensed location and subsequent actual location, the assessment is used to select a new virtual location for the virtual probe.

12 Claims, 6 Drawing Sheets

(a)

(b)

SYSTEMS, METHODS AND DEVICES FOR CORRELATING REFERENCE LOCATIONS USING IMAGE DATA

RELATED PATENT DOCUMENTS

This patent document claims the benefit, under 35 U.S.C. §119(e), of U.S. Provisional Patent Application Ser. No. 61/125,309 filed on Apr. 23, 2008 and entitled "Incremental method for registering electroanatomic mapping data to surface mesh models of the left atrium;" this patent document is fully incorporated herein by reference.

FIELD OF THE INVENTION

The present invention relates to correlating reference locations using image data. As many aspects of the example embodiments disclosed herein relate to and significantly build upon previous developments in this field, the following discussion summarizes such previous developments to provide a solid understanding of the foundation and underlying teachings from which implementation details and modifications might be drawn. It is in this context that the following discussion is provided and with the teachings of the references incorporated herein by reference.

BACKGROUND

Traditional surgery methods involve incisions that allow a surgeon direct access to the part of the body that is to be operated upon. While this can offer the benefit of direct visual and/or tactile feedback to the surgeon, the procedure can be relatively evasive. For instance, correction of abnormalities of the heart is accomplished by cutting through bones and muscle of the chest. This leads to a long and painful recovery that stems as much or more from the side effects of the opening the chest as from the work on the heart itself.

A set of relatively new techniques have shown significant promise in alleviating much of the trauma often associated with traditional surgery methods. These techniques involve small incisions and are often referred to as Minimally Invasive Surgery (MIS). Using specialized techniques surgeons perform surgery through the small incisions. For example, specially designed probes (e.g., catheters) can be introduced to the heart by feeding the probe through a vein. The surgeon manipulates the probe near a desired location to perform the necessary action, such as ablation of abnormal tissue.

An important component of MIS is the ability of the surgeon to properly maneuver the probes to the desired locations. The surgeon cannot directly see the inserted probe and its position within the patient. Thus, a number of different imaging modalities can be used to guide placement of the probe. Competing with the desire for accurate guidance is the desire for small probe size, fast procedures, simplicity and reduced costs. One method that has gained relatively wide acceptance is an electroanatomic mapping system (EMS). An EMS uses one or more electrical probes for which three-dimensional positioning information can be determined relative to a reference point, such as a reference patch placed external to the patient. The positioning information is then correlated to the internal structure of the patient. While this procedure has seen a wide degree of success, a number of problems and difficulties hamper the true potential of these and related procedures.

SUMMARY

Aspects of the present invention are exemplified in a number of illustrated implementations and applications, some of which are shown in the figures and characterized in the claims section that follows. Certain embodiments of the present invention are directed to coordination of multiple reference points using image data taken from structures where views may be otherwise obstructed.

According to one specific embodiment of the present invention, a method is implemented using a circuit. The method is for use with an actual probe within an anatomical structure. For a virtual probe at a virtual location within a model of the anatomical structure, the circuit generates virtual image data captured by the virtual probe. The circuit assesses the virtual image data through a probabilistic comparison of the virtual image data to actual image data captured by the actual probe at an actual location. Based upon the assessment, the circuit updates a correlation between the actual location of the actual probe and a sensed location of the actual probe to provide synchronicity between the sensed location and actual location. For maintaining the synchronicity between a subsequently sensed location and subsequent actual location, the circuit uses the assessment to select a new virtual location for the virtual probe.

According to another embodiment of the present invention, a system is implemented which includes a circuit configured and arranged to implement a number of steps. For a virtual probe at a virtual location within a model of the anatomical structure, the circuit generates virtual image data captured by the virtual probe. The circuit assesses the virtual image data through a probabilistic comparison of the virtual image data to actual image data captured by the actual probe at an actual location. Based upon the assessment, the circuit updates a correlation between the actual location of the actual probe and a sensed location of the actual probe to provide synchronicity between the sensed location and actual location. For maintaining the synchronicity between a subsequently sensed location and subsequent actual location, the circuit uses the assessment to select a new virtual location for the virtual probe.

According to another embodiment of the present invention, a circuit-implemented method correlates an actual reference point to a virtual reference point corresponding to a surface mesh model of an anatomical structure. For a probe with a known position relative to the actual reference point, a set of virtual poses are selected relative to the virtual reference point as a function of virtual pose weights. For the virtual poses, virtual image data is created by applying the virtual poses to the model. Correlation scores to the virtual poses are created as a function of correlation between the captured image data and the virtual image data. The virtual pose weights are updated as a function of the correlation scores.

Consistent with another example embodiment, a computer-readable medium is programmed with instructions that when executed by a processor perform a number of steps. For a virtual probe at a virtual location within a model of the anatomical structure, the processor generates virtual image data captured by the virtual probe. The processor assesses the virtual image data through a probabilistic comparison of the virtual image data to actual image data captured by the actual probe at an actual location. Based upon the assessment, the processor updates a correlation between the actual location of the actual probe and a sensed location of the actual probe to provide synchronicity between the sensed location and actual location. For maintaining the synchronicity between a subsequently sensed location and subsequent actual location, the processor uses the assessment to select a new virtual location for the virtual probe.

The above summary is limited to characterizing certain aspects and is not intended to describe each illustrated embodiment or every implementation of the present invention. The figures and detailed description that follow, including that described in the appended claims, more particularly exemplify these embodiments.

BRIEF DESCRIPTION OF THE DRAWINGS

The invention may be more completely understood in consideration of the detailed description of various embodiments of the invention that follows in connection with the accompanying drawings as follows.

Figure 1:
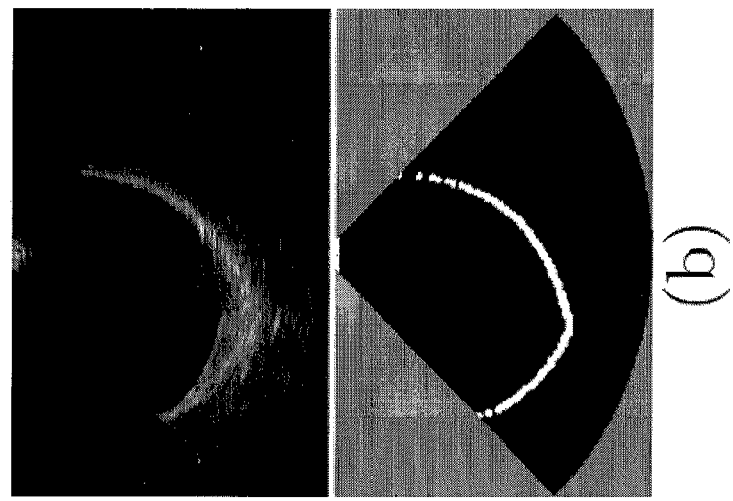
FIG. 1A shows a diagram showing various reference points relative to an anatomic structure, a probe and the image capture area for the probe, consistent with an embodiment of the present invention.
FIG. 1B shows a comparison of actual image data to virtual image data, consistent with an embodiment of the present invention.
Figure 1:
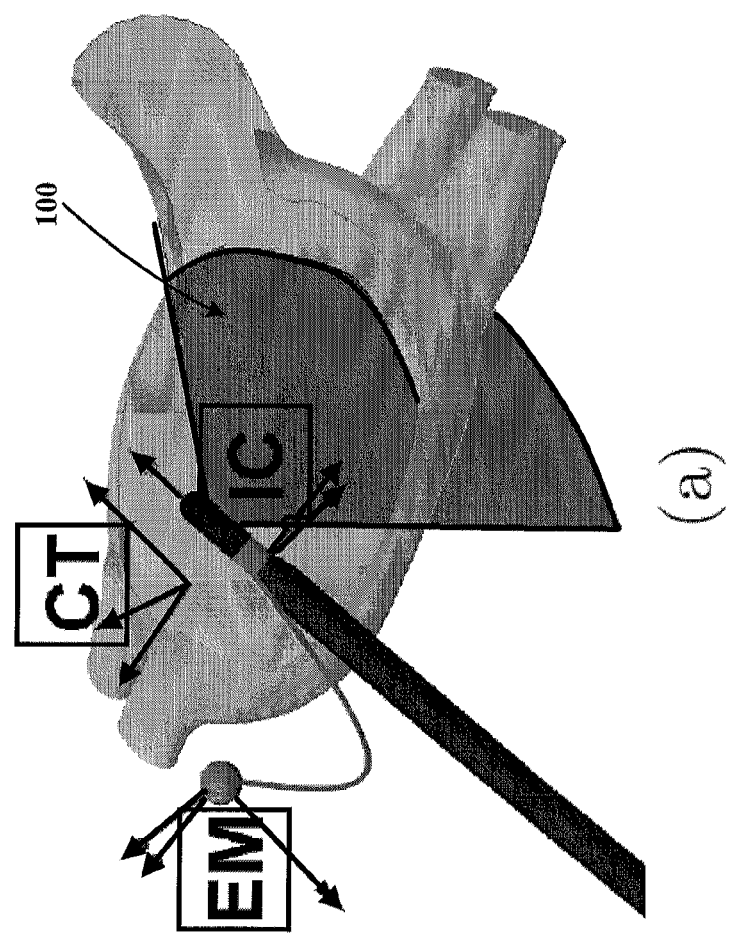

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for certain image-coordinate mapping, and has been found to be particularly advantageous for minimal-invasive surgery (MIS) techniques that use coordinate mapping between an actual reference location and a virtual reference location. While the present invention is not necessarily limited to such applications, various aspects of the invention may be appreciated through a discussion of various examples using this context.

As a first example, an embodiment of the present invention is directed to an automated system that translates coordinates for mapping an actual representation of a structure to coordinates for mapping relative to a sensed reference point. To determine the translation parameters, a virtual representation of a structure is generated of an anatomical structure. A virtual coordinate system and actual image data are used to estimate the location of the probe relative to the actual structure. A position detection device provides sensed position information of a probe relative to an actual reference point. The position detection device is capable of tracking the location of the probe using a sensor system as a function of a reference point. Specialized algorithms, discussed in more detail herein, use image data captured by the probe to estimate the actual position of the probe within the structure. The estimated position can then be translated to the sensed position. This translation is then used with data from the position detection device to determine the location of the probe within the structure. The algorithms allow for tracking of the probe as it is moved and are surprisingly fast at developing a translation.

Certain aspects of the present invention can be particularly useful for compensating for changes in the location of anatomical structure relative to the sensed position referenced to an actual location. These changes can occur due to movements of the patient, unreliable position sensor data or other factors.

In other examples, specific embodiments of the present invention involve the use of a probe (e.g., a catheter) as part of a procedure, such as Minimally-Invasive Surgery (MIS). The probe includes imaging technology to capture images of the anatomical structure. The type of imaging technology is not limited by the present invention; however, aspects of the present invention have been shown to be surprisingly accurate when used with relatively simplistic imaging technologies. For instance, two-dimensional ultrasound imaging can be used to generate image data that is then used to determine the location of the probe within the anatomical structure.

In other specific example embodiments, the invention involves correlating captured image data with a virtual representation of the anatomical structure. A proposed position and orientation of the probe is used to generate a virtual image of the anatomical structure. Assuming the virtual representation is accurate, the correlation between the virtual image and the actual image should be high when the proposed position and orientation match that of the actual position and orientation. A brute force method of correlation is used to assess the correlations for each possible position and orientation for the probe. As the resolution of the tracking algorithm increases the accuracy of the tracking system increases; however, the number of potential positions and orientations, sometimes referred to as potential poses, also increases. For relatively high tracking resolutions, calculating the correlation for each potential position becomes prohibitively high. Thus, there is a competing tension between highly accurate tracking, fast tracking and required computational power. Aspects of the present invention are particularly useful for providing high resolution tracking using efficient algorithms. These algorithms provide mechanisms for fast converging solutions that provide high-resolution solutions. In particular embodiments of the present invention, virtual images for a subset of all potential poses are correlated with the actual image. Intelligent algorithms use probability estimates to steer the correlation efforts toward the most probable poses.

In yet other specific example embodiments, aspects of the present invention are directed toward compensation for drift of the relative positions of the anatomical structure and the actual reference point of the position determining device. The drifts between the two devices can be caused by a number of factors, such as patient breathing and other movements or changes in the sensed position data. For instance, electroanatomic mapping systems (EMS) often use a reference patch that is fixed to the patient's chest or back. An EMS functions by detecting changes in electromagnetic fields caused by a probe located within the patient. The reference patch serves to provide a reference point. The EMS determines the location of the probe as a function of the reference patch. Thus, if the reference patch is not fixed relative to the internal anatomical structures of the patient, the location information provided by the EMS is difficult to correlate with the internal structures. For example, breathing changes the size and shape of the chest cavity, which results in movement and shifting of internal structures relative to an externally applied reference patch. Aspects of the present invention are particularly useful for providing surprisingly resiliency to such movements, while also providing fast convergence to accurate translation estimates. Yet another issue with EMS occurs due to the dependence upon magnetic fields. Ferromagnetic objects can disrupt these magnetic fields and thereby shift the relative sensed position of the probe. Unless otherwise stated, movement of the reference refers to any change in the correlation between a sensed location and the actual location within the anatomical structure.

Aspects of the present invention are particularly useful for use with EMS probes and for addressing relative movement of the reference, e.g., due to patient movements. This movement can cause shifting in the coordinates of recorded points. EMS can be implemented using a location pad that generates magnetic fields. The tip of the ablation catheter is tracked as a function of these magnetic fields allowing for display of the probe's position in real-time on a monitor. The mapping catheter and reference patch are communicatively coupled to a recording system. The data stored in the recording system and obtained from the reference pad and probe is analyzed to determine the location of the mapping probe. The mapping probe can be moved along the outside of the anatomical structure while location points are stored as a point cloud. The point cloud can then be used to generate a map of the structure using the anatomical and/or electrophysiological data. Movement that occurs during generation of the point cloud can corrupt the mapping locations requiring that the mapping process be started anew. This can be frustrating as data collection often takes up to an hour, and is complex enough to warrant constant supervision. Embodiments of the present invention allow for the synchronicity between the sensed position and the actual position of the probe to be maintained in real-time.

Aspects of the present invention have been shown to be surprisingly effective and flexible. The various example embodiments and test results show effective and fast calculation of offsets between actual locations and sensed locations. The robust nature allows for the use of relatively simple imaging technology and also for relatively simply image correlation techniques. For instance, embodiments of the present invention have been shown to be effective for two-dimensional ultrasound imaging. This ultrasound imaging is subject to noise and often produces images without clearly defined surfaces. Surprisingly, embodiments of the present invention were shown to accurately track the position of a probe within a structure using these types of images. Moreover, the image correlation was implemented using relatively simplistic bit-wise operations. While the invention is not limited to these specific types of imaging techniques, the flexibility and effectiveness in this context can be particularly useful for a number of applications.

Other embodiments of the present invention allow for the use of three dimensional or even four dimensional image data. Three dimensional image data can be provided by a number of different mechanisms including, but not limited to, an image capture device capable of providing a three dimensional image data or by merging a set of two dimensional images. The additional dimension provides additional image data that can be used to further define the correlation determination between virtual image data generated by a model and the actual image data. Four dimensional images use traditional three dimensional data (x,y,z) but can add an additional dimension to the model. In one example, the extra dimension can represent possible movements of the structure. For instance, a model of the heart can include modeling of the various states of the heart as it contracts to pump blood through the body. This extra movement-dimension can therefore help increase the accuracy of the correlation by properly modeling moving anatomical parts.

While embodiments of the present invention have been shown to be effective with a relatively simple technique to correlate virtual images with actual images, a number of other techniques could be used. A few example techniques include, but are not limited to, identification and use of surfaces and feature mapping of the structure. For instance, feature mapping could be used as a registration technique to ensure the general orientation of the probe is correct or to fine tune the position determination. For a general orientation, a prominent feature that is easily distinguishable can be used, even where the feature is not particularly useful for defining the specific location. For example, the structure may have a number of features that are relatively similar to one another. Even where identification of these features does not distinguish one feature from another, the features could provide other position information, such as rotational/orientation data. This could be particularly useful for initializing values (e.g., probability weights) used in the algorithms. For more of a fine-tuning application, feature mapping could be used to verify or otherwise modify a determined position. As feature mapping can often require a significant amount of processing power and/or time, the feature mapping could be done periodically and/or limited to feature detection that corresponds to the currently identified actual location. This type of periodic fine-tuning can be particularly useful for avoiding the algorithms from being trapped at a local minimum. For instance, feature mapping could provide data that indicates the current location is offset by a relatively small amount. The algorithm could be modified to reflect this small offset thereby moving away from the local minimum and towards the true location.

While embodiments of the present invention are believed to be particularly useful for cardiac-based MIS and more particularly to ablation, a variety of other implementations are also possible. A few non-limiting examples include placement of stents, cardiac repair (e.g., valve repairs), placement of pacemaker leads and MIS in other parts of the body.

As discussed herein, various embodiments of the present invention have been shown to be particularly useful for real-time positioning and image display. Various embodiments can be used to generate an image of the anatomical structure and to show the probe location within the image. A surgeon can guide the probe by viewing the generated image, which can display the probe location in real-time. Different applications have different time-based considerations for how fast the probe location needs to be determined and/or updated. For instance, cardiac implementations can be subject to relatively rapid movements of the ventricles or atria. Other anatomical areas may not have as stringent of requirements. Thus, the responsiveness of the tracking can be adjusted accordingly while maintaining sufficient synchronicity between a sensed position and the estimated actual position.

Turning now to a few specific implementations of the present invention, FIGS. 1-5 are discussed in connection with an embodiment useful in MIS-based in cardiac applications. While the invention is not limited thereto, an understanding of various aspects of the invention can be appreciated in this context. FIG. 1(*a*) shows reference frames assigned to the EMS (EM), intracardiac echo (ICE) catheter tip (IC) and Computed Tomography/Magnetic Resonance (CT/MR)-based surface mesh (CT). A computer or circuit implemented algorithm compares ICE data to the surface mesh, thereby implicitly assuming that the mesh represents the left atrium. The field of view 100 for the probe indicates the portion of the structure for which the probe will capture image data.

In specific algorithmic implementation, affine transformations are used to relate coordinates between reference frames A and B with the following notation:

$$^AT^B = \begin{bmatrix} ^AR^B & ^AO^B \\ 000 & 1 \end{bmatrix}, \quad (1)$$

$$^AT^B \in \Re^{4\times 4}$$

where $^AR^B \in \Re^{3\times3}$ is the coordinate axes rotation offset, and $^AO^B \in \Re^{3\times1}$ is the coordinate original offset. $^AT^B$ is represented by its pose vector:

$$^AP^B = [x,y,z,\alpha,\beta,\gamma]^T, \; ^AP^B \in \Re^{6\times1} \quad (2)$$

where $[x,y,z]^T = {}^AO^B$ and $(\alpha,\beta,\gamma)$ are the xyz Euler angles describing $^AR^B$. Finally, a function $h_{P\to T}$ is defined so as to convert $^AP^B$ into $^AT^B$:

$$h_{P\to T} = \begin{bmatrix} & & & x \\ R_z(\alpha)\cdot R_y(\beta)\cdot R_x(\gamma) & & y \\ & & & z \\ 0 & 0 & 0 & 1 \end{bmatrix}, \quad (3)$$

$$h_{P\to T} \in \Re^{6\times1 \to 4\times4}$$

With corresponding inverse $h_{T\to P}$.

A Recursive Bayesian State Estimation (RBSE) framework is implemented to provide an incremental registration algorithm. The general RBSE models are as follows: at time step k, the estimate of the systems state is defined as $p(x_k|u_{1:k}, z_{1:k})$, the probability distribution over all possible states $x_k$ conditioned on all past controls $u_{1:k}$ and measurements, $z_{1:k}$. For further details and background information relating to conditioning of a probability distribution over all possible states reference can be made to, Thrun, S.: *Probabilistic algorithms in robotics*. AI Magazine 21(4), 93-109 (2000), which is fully incorporated herein by reference. Here, $x \in \Re^{6\times1}$ is the pose of the ICE catheter with respect to the left atrium, $u \in \Re^{4\times4}$ is the transformation in ICE catheter pose detected by the EMS, and $z \in \Re^{n\times m}$ is the acquired ICE image of size n×m pixels. Using reference frame notation, the state and control input are defined as follows:

$$x_k = {}^{CT}P_k^{IC} \; u_k = {}^{IC}T_{k-1}^{EM,EM}T_k^{IC} \quad (4)$$

By treating $u_k$ as a differential measurement out unmodeled drifting of the EMS reference frame can be factored out assuming the sampling frequency is substantially faster than the drifting modes.

At time step k, the state evolution can be predicted using the equation:

$$x_k = f(x_{k-1}, u_k, q_k) \quad (5)$$
$$= h_{T\to P}(h_{P\to T}(x_{k-1}) \cdot {}^{IC}T_{k-1}^{EM} \cdot {}^{EM}T_k^{IC}) + q_k$$

with process noise $q_k \in \Re^{6\times1}$, and the measurement is estimated as:

$$y_k = g_{ice}(x_k, T_k), \; y_k \in \Re^{n\times m} \quad (6)$$

with measurement noise $r_k \in \Re^{n\times m}$. Function $g_{ice}$ generates a virtual ICE image ($y_k$) of the surface mesh as it would appear if taken from pose $x_k$ (FIG. 1(*b*)). Acquired ICE image $z_k$ is compared to $y_k$ using a normalized mutual information (NMI) correlation metric. For further information and background details on an example implementation of an NMI correlation metric reference can be made to Pluim, J. P., Maintz, J. A., Viergever, M. A.: *Mutual-information-based registration of medical images: A survey*. IEEE Transactions on Medical Imaging 22(8), 986-1004 (2003), which is fully incorporated herein by reference.

Eqns. 5 and 6 are non-linear and Eqn. 6 cannot be defined analytically, and therefore, one implementation of the present invention uses an unscented particle filter (UPF) within the RBSE technique. The UPF is particularly useful for state estimation problems that are highly nonlinear and do not yield Gaussian state posteriors. Instead, the UPF represents state posteriors using several "particles" sampled over the distribution. For further information and background details on general aspects of an UPF reference can be made to Rui, Y., Chen, Y.: *Better proposal distributions: object tracking using unscented particle filter*. In: Proceedings of the IEEE Computer Society Conference on Computer Vision and Pattern Recognition, vol. 2, pp. 786-793 (2001), which is fully incorporated herein by reference.

Each particle in the UPF implementation is initially assigned a random pose $x_O = {}^{CT}P^{IC}$ taken from a uniform distribution over all possible poses, the range of which is assumed to be slightly larger than the size of an adult left atrium:

$$\text{Range}({}^{CT}P^{IC}) = \text{Range}([x, y, z, \alpha, \beta, \gamma]^T) \quad (7)$$
$$= [\pm 50 \text{ mm}, \pm 50 \text{ mm}, \pm 50 \text{ mm}, \pm$$
$$180°, \pm 90°, \pm 180°]^T$$

Figure 2:
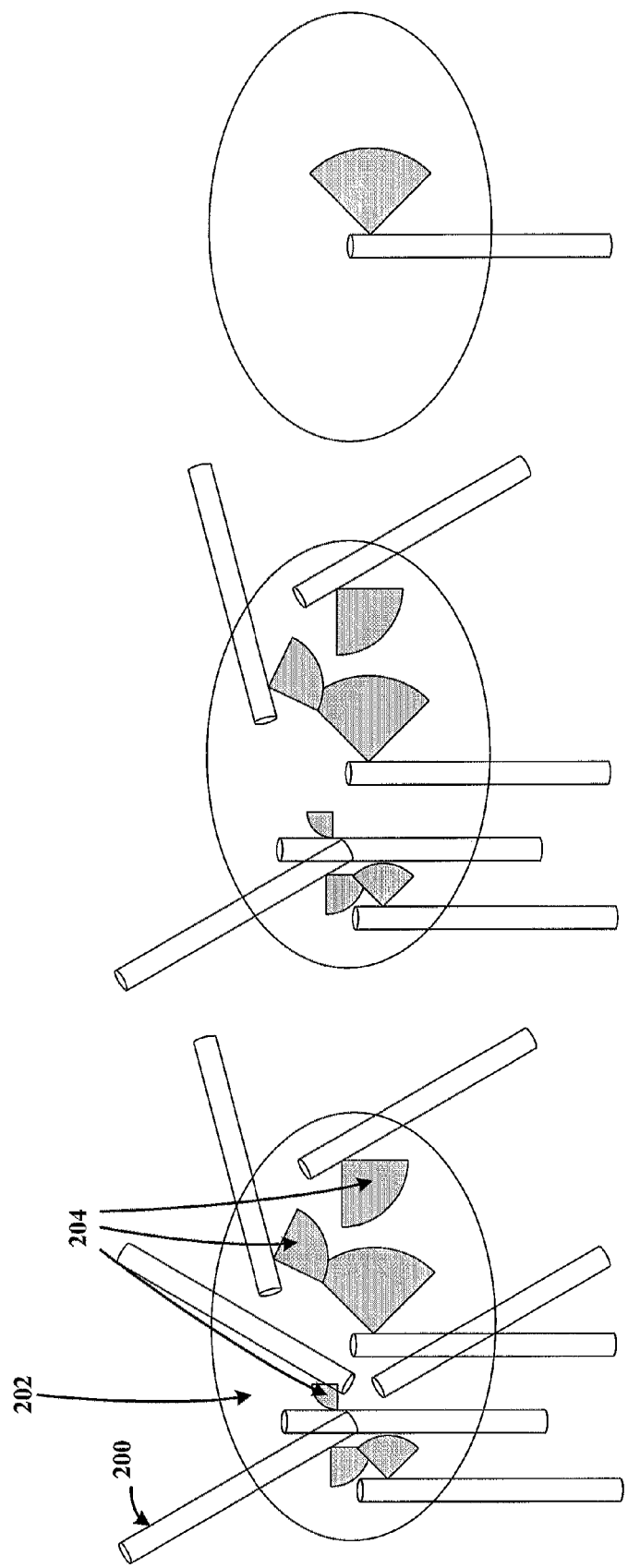
FIG. 2 shows a conceptual representation of a number of potential poses represented by virtual probes within a model, consistent with an embodiment of the present invention.
Figure 3:
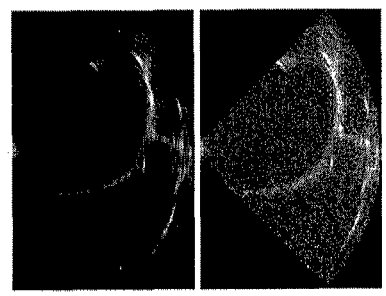
FIG. 3A shows the components used in the experimental setup, which includes an intracardiac echo (ICE) catheter tip in position for imaging the left atrium phantom, consistent with an embodiment of the present invention.
FIG. 3B shows the imaged volume swept out by rotating an ICE catheter while acquiring data, consistent with an embodiment of the present invention.
FIG. 3C shows the Gaussian noise added to acquired ICE images before thresholding to binary, consistent with an embodiment of the present invention.
Figure 3:
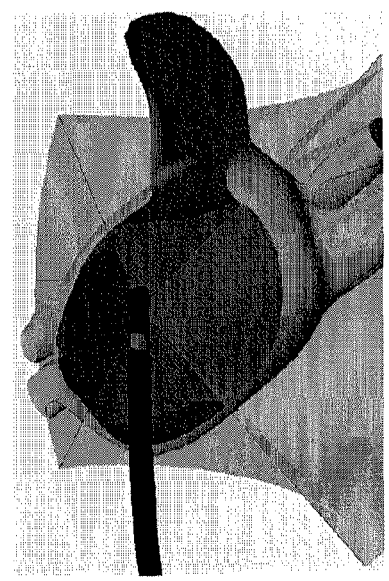
Figure 3:
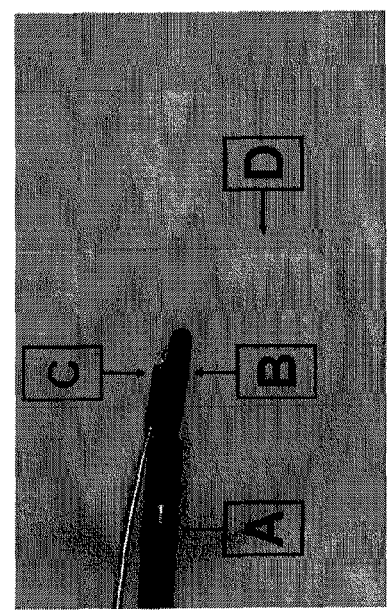

After all particles have undergone state evolution, they are weighted using their NMI correlation score and re-sampled using stochastic universal sampling. For further details on re-sampling using stochastic universal sampling reference can be made to Baker, J. E.: *Reducing bias and inefficiency in the selection algorithm*. In: Proceedings of the Second International Conference on Genetic Algorithms and their Application, pp. 14-21 (1987), which is fully incorporated herein by reference. Particles yielding virtual ICE images with low correlation scores are discarded and eventually only a few particles, whose estimates are close to the actual state, remain in consideration. FIG. 2 shows a conceptual representation of a number of potential poses represented by each of the virtual probes 200 within the model 202. The virtual image data generated for each pose is represented by the field-of-view 204 spanning from the virtual probes 200. As shown, from left to right, the number of proposed virtual poses is reduced as the confidence in the proposed poses increases. To speed up or otherwise simplify the comparison, ICE images can be converted to a binary representation, so that all comparisons between real/actual images and virtual images can be performed using bit-wise operations. Certain implementations also include decimating the resolution of the acquired ICE image when there are a large number of particles to consider, and gradually returning to the native resolution as the algorithm converges upon a solution.

The UPF implementation generates an estimate of $^{CT}P^{IC}$, which is then used to recover $^{CT}T_k^{EM}$. This recovery can be implemented in a number of ways. If it is assumed that that $^{CT}T^{EM}$ may change over time; that is the EMS reference frame may move without our knowledge, then the following equation can be used:

$$^{CT}T_k^{EM} = h_{P \to T}(^{CT}P_k^{IC}) \cdot ^{IC}T_k^{EM} \quad (8)$$

However, if it is assumed that $^{CT}T^{EM}$ will change relatively slowly, then a least-squares estimate of $^{CT}T_k^{EM}$ can be computed by considering the last n UPF estimates simultaneously. Increasing n leads to a more stable estimate, but at the expense of increased sensitivity to EMS reference frame drifting.

The surprising performance characteristic of these implementations of the registration algorithms performance were measured using left atrium phantom cast in a silicone compound that readily images under ultrasound. An ICE catheter was rotated about its longitudinal axis while continuously acquiring cross sectional images of the phantom. The catheter was rotated using a motorized system that commanded a 60°, $\frac{1}{12}$ Hz sine wave trajectory. Images were acquired at 10 Hz, or roughly every 2° at the peak rotation velocity. The ICE catheter transducer was not calibrated to produce spatial distortions in its images, which emulate a source of measurement noise.

A 6DOF position/orientation sensor (Ascension Technology Corp., Burlington, Vt.) was attached to the ICE catheters tip to monitor its exact position and orientation over time. A second sensor was affixed to the phantom at a known position and orientation allowing us to measure $^{CT}T^{EM}$ for validation. FIG. 3(a) shows the components used in the experimental setup, which includes the ICE catheter tip in position for imaging the left atrium phantom. FIG. 3(b) shows the imaged volume swept out by rotating the ICE catheter while acquiring data.

In addition to testing the algorithms accuracy under the stationary conditions described above, a separate test was performed in which the EMS reference frame was slowly moved by translations of $\leq 20$ mm along each axis, and rotations of $<10°$ about each axis, to emulate sensor drift caused by breathing or patient movement. The translation drift speed was capped at $$\frac{1 \text{ mm}}{\text{sec}},$$

and rotation drift speed at $$\frac{1°}{\text{sec}}.$$

To ensure the robustness of the NMI-based mage correlation algorithm, a third test was performed in which Gaussian noise ($\mu=0.2$, $\sigma=0.25$) was added to the acquired ICE images before thresholding to binary (FIG. 3(c)). The amount of noise added was chosen based on the threshold after which ultrasound reflections were completely obscured in the images.

Table 1 shows registration errors with stationary EMS reference frame.

| Measured Error | 1 Sweep | 2 Sweeps | 3 Sweeps | 4 Sweeps |
| --- | --- | --- | --- | --- |
| "Clean" Position Error | μ = 3.38 mm | μ = 1.01 mm | μ = 0.80 mm | μ = 0.74 mm |
|  | σ = 2.33 mm | σ = 0.56 mm | σ = 0.39 mm | σ = 0.33 mm |
| "Clean" Orientation Error | μ = 12.3° | μ = 2.77° | μ = 2.33° | μ = 2.22° |
|  | σ = 8.21° | σ = 1.63° | σ = 0.90° | σ = 0.84° |
| "Noisy" Position Error | μ = 3.99 mm | μ = 2.29 mm | μ = 1.90 mm | μ = 1.86 mm |
|  | σ = 2.49 mm | σ = 1.93 mm | σ = 1.50 mm | σ = 1.30 mm |
| "Noisy" Orientation Error | μ = 17.3° | μ = 8.27° | μ = 5.82° | μ = 5.13° |
|  | σ = 11.4° | σ = 7.43° | σ = 3.94° | σ = 2.46° |

Holding the EMS reference frame stationary, the registration algorithm's accuracy was tested as the ICE catheter was rotated through its full extent four times (over 48 seconds). A least squares estimate of $^{CT}T_k^{EM}$ was computed and the accuracy of the estimate after each sweep over 100 separate trials was measured. This experiment was repeated, once using "clean" ICE images and once using "noisy" ICE images. Table 1 shows the mean and standard deviation of error in the registration algorithms estimate after each sweep. Two quantities were computed: registration position error and orientation error. The position error is measured as the Euclidean distance between the actual and estimated coordinate origin offset, $\|^{CT}O_{act}^{EM} - ^{CT}O_{est}^{EM}\|$ and the orientation error is measured as the minimum angle required to transform $^{CT}R_{est}^{EM}$ into $^{CT}R_{act}^{EM}$ using an angle-axis rotation scheme. The accuracy improves with continued imaging, and, using both "clean" and "noisy" images, the estimate's error falls below 2 mm and 6° after considering four sweeps of data.

The registration algorithms accuracy was also tested while moving the EMS reference frame. $^{CT}T_k^{EM}$ was computed using Eqn. 8 and the accuracy of the estimate was measured over 100 separate trials. This test was performed once using "clean" ICE images and once using "noisy" ICE images.

Figure 4:
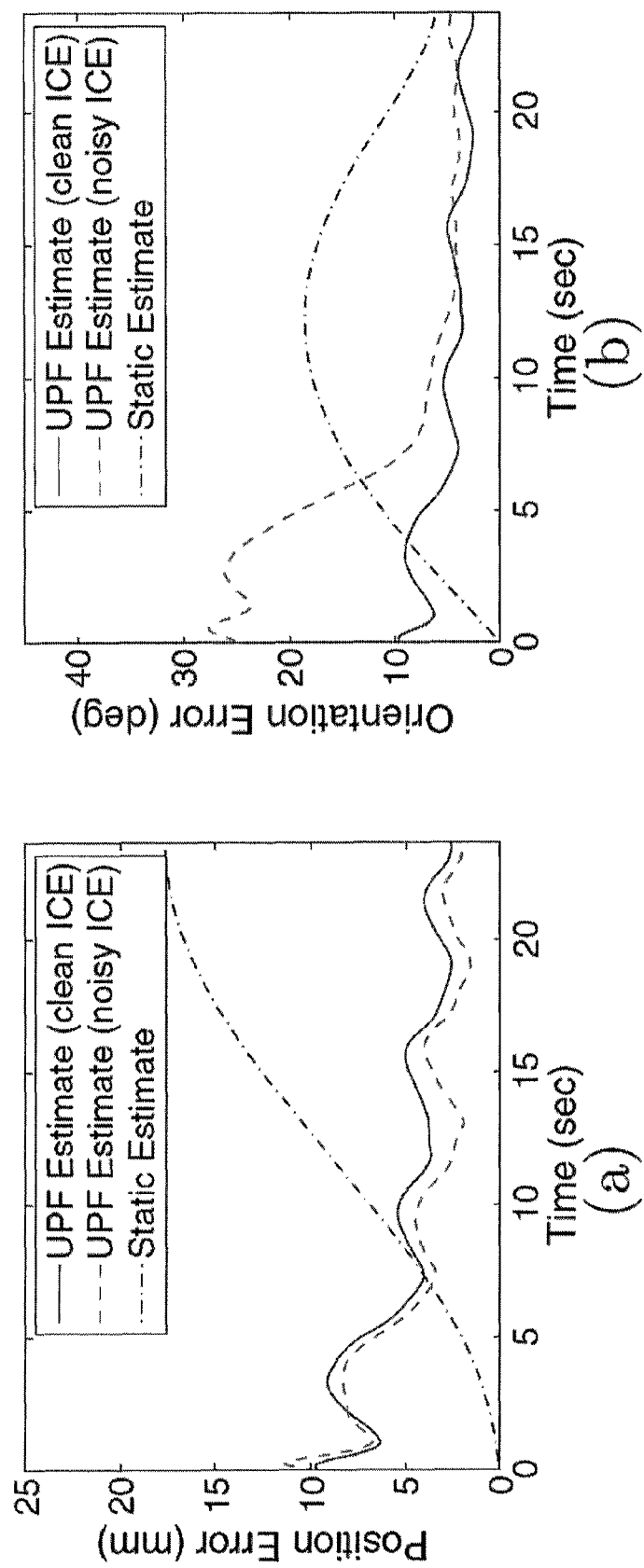
FIG. 4A depicts a plot charting the average position errors of the registration estimate over time, consistent with an embodiment of the present invention.
FIG. 4B depicts a plot charting the average orientation errors of the registration estimate over time, consistent with an embodiment of the present invention.

FIG. 4 depicts two plots charting the average position and orientation errors of the registration estimate over time. The duration shown is equivalent to two rotation sweeps. After one sweep, the mean position error drops below 5 mm in both the "clean" and noisy" case, and after two sweeps the position error stays roughly around 2.5 mm. Similarly, the orientation error drops below 10° after one sweep, and below 5° after two sweeps. Comparisons were preformed between the results and a "static" estimation scheme, where $^{CT}T_k^{EM}$ is assumed constant over time. The static schemes estimate were set to $^{CT}T_{actO}^{EM}$, so that initially there is no error in its estimate. As the EMS reference frame drifts back and forth, the static scheme's performance is inversely proportional to the amount of drift. By the end of two sweeps, the average position error in the static estimate is greater than 15 mm. This would be worse if the static scheme's estimate was not initialized to $^{CT}T_{actO}^{EM}$.

Figure 5:
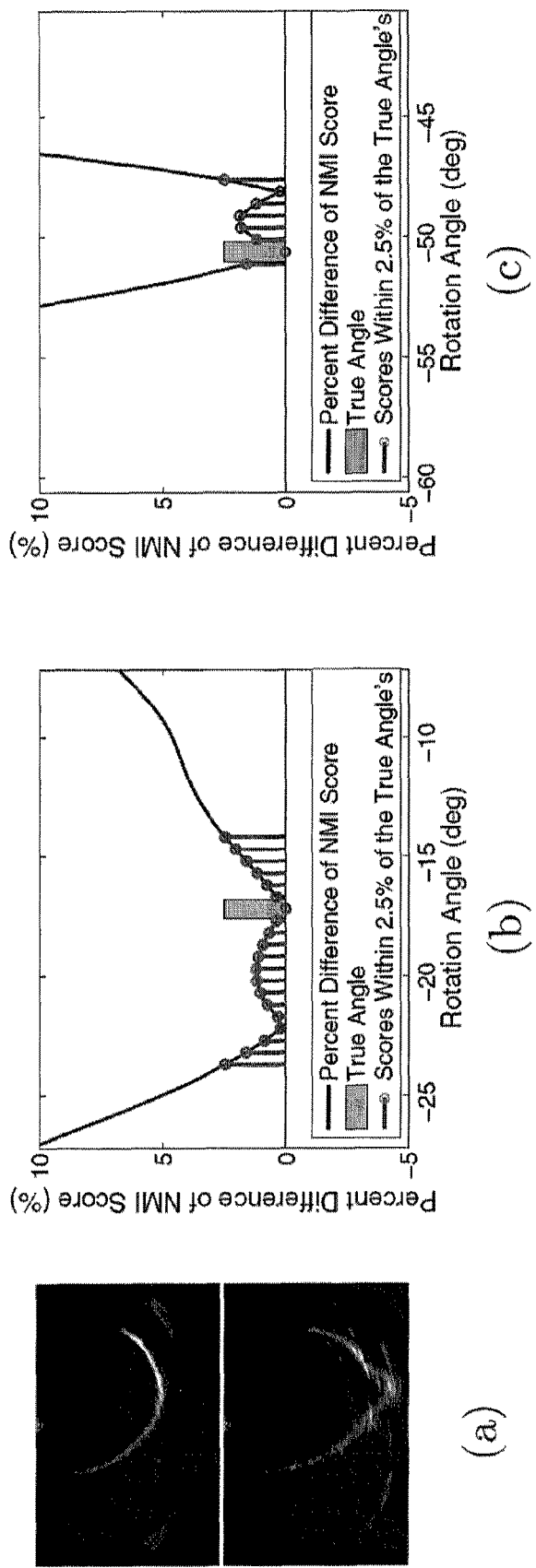
FIG. 5A shows ICE images of the anatomical center (top) and the pulmonary veins (bottom), consistent with an embodiment of the present invention.
FIG. 5B shows normalized mutual information (NMI) score percent-differentials for neighboring angles that also image the anatomical center, consistent with an embodiment of the present invention.
FIG. 5C shows NMI score percent-differentials for neighboring angles that also image the veins, consistent with an embodiment of the present invention.

The ability to estimate the correct registration parameters can be affected by the resolution of the NMI correlator and also by the region of the anatomy currently being imaged. FIG. 5 highlights uncertainty when imaging two different regions of the anatomy and also shows results for the surprising accuracy and effectiveness of embodiments of the present invention. When imaging the mostly-uniform anatomical center, the range of angles generating NMI scores within 2.5% of the score at the true orientation angle is 10°. When imaging the feature-rich region surrounding the veins, however, this range drops to 5°. Consequently, the uncertainty increases when the ICE catheter sweeps through the anatomical center, qualifying the oscillatory behavior seen in the estimate error (FIG. 4). FIGS. 5(b) and 5(c) also reveal that our NMI correlator can suffer from local minima. Moving towards these minima can be avoided based on knowledge of a current estimate and rotation command. However, it is still possible to be trapped by a minimum that is closer to the current estimate than the true state.

Figure 6:
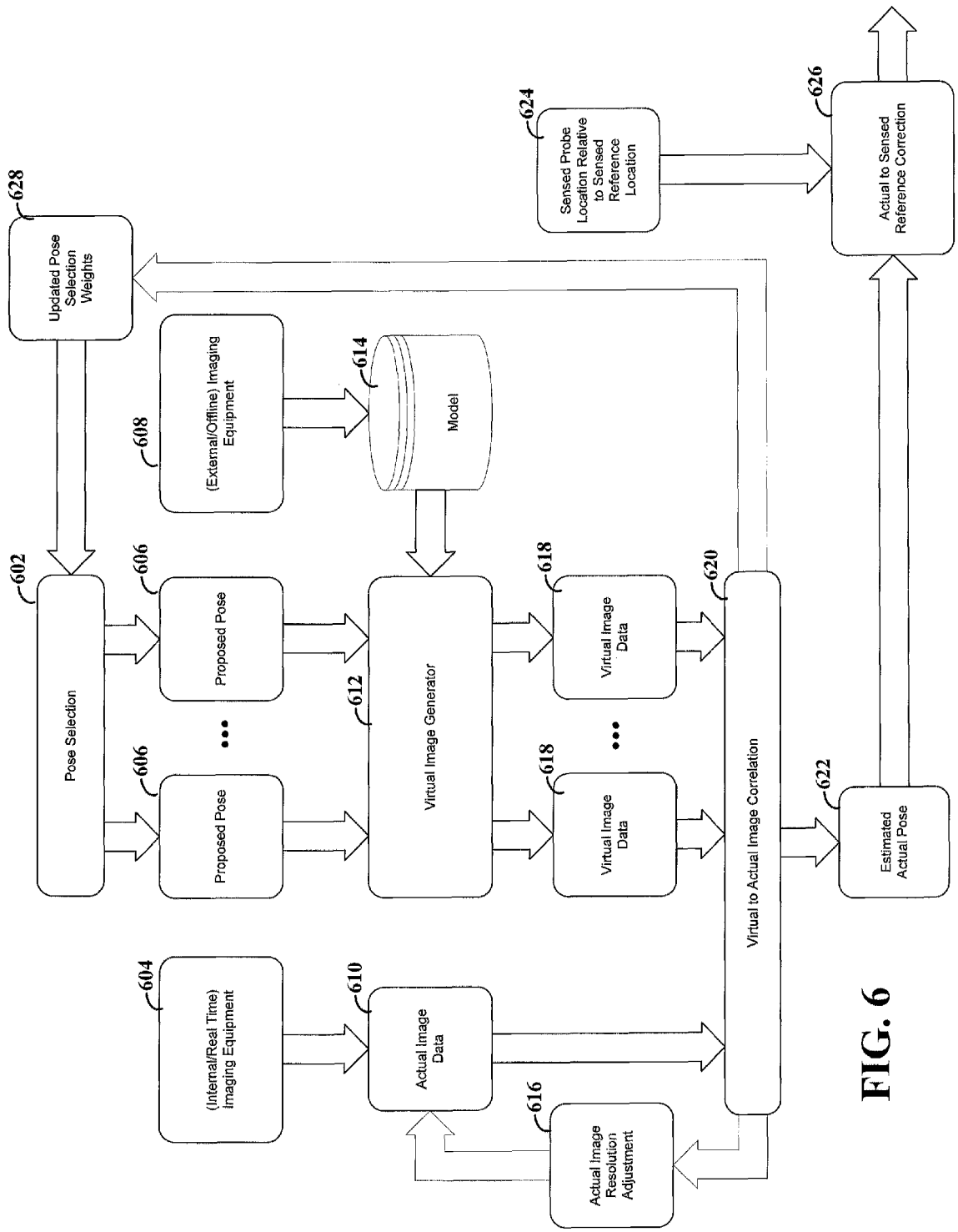
FIG. 6 depicts a flow diagram for correlating reference locations, consistent with an example embodiment of the present invention.

FIG. 6 depicts a flow diagram, consistent with an example embodiment of the present invention. Pose selection 602 produces one or more proposed poses 606. The poses 606 represent data used to define the position of the probe and sufficient to ascertain the portion of the anatomical structure that would be captured by the imaging sensor of the probe. For instance, the poses can be represented by positional data and orientation data. The selection of the poses 606 can be made according to a weighted scoring for the poses designed to select those poses that have a higher probability of being correct. In some instances, such as early in the registration process, there may be little or no weight afforded to this selection process (e.g., selection of each pose is equally likely). As additional data is provided and the confidence in the estimated position increases, the weight factors can be adjusted accordingly and the probability of selecting certain poses will be modified accordingly.

A virtual image generator 612 uses model data 614 to generate virtual image data 618 for the poses 606. The model can be generated by a number of suitable techniques 608 including, but not limited to imaging equipment used prior to the insertion of the probe. It is also possible that the model is generated from information other than imaging equipment. For instance, a generic model of the anatomical structure can be used, thereby removing the need to image the anatomical structure for each patient. The generic model could represent the common morphology of the anatomical structure. Modifications to such a generic model could be made for the particular patient based upon a number of inputs, such as age, size and the like.

The probe includes imaging equipment 604 which generates actual image data 610. The virtual image data 618 is compared to the actual image data to determine a correlation 620 therebetween. This correlation can be used to update the pose selection weights 628 and to produce an estimation of the actual pose 622. As confidence in the estimated actual pose 622 increases, the resolution of the actual image 610 can be increased 616.

The estimated actual pose 622 is correlated with the sensed location 624 to provide a correlation 626 between the actual location of the probe and the sensed location of the probe.

According to one embodiment of the present invention, a circuit-based system provides the functionality described herein. This circuit-based system receives data from a position sensor and from actual images of one or more probes. The flexibility of the algorithms and implementations allows for a wide range of different probes and position sensors to be used. In one implementation, the system configures the algorithms according to the specific probe and positional sensor being used according to predetermined settings for the specific devices. According to another implementation, the probes and/or positional sensor provide configuration data to the system that is used to define the settings for the algorithms. This allows for manufactures of various probes and position sensors to control their device parameters without the need for the system manufacturer to coordinate with each probe/sensor manufacturer. A probe/sensor manufacturer can store the relevant specifications on a nonvolatile memory. This nonvolatile memory can be read by the system when the probe or position sensor is connected to the system. In another implementation, the system can automatically calibrate for a specific probe and/or position sensor. As an example, a calibration device could be provided in which the probe is inserted and tracked by the position sensor. The system would use the calibration information to develop the parameters for the particular probe and position sensor. Another implementation allows for selection of the specific probe type by an operator of the system. The probe types can be selected from a predefined list of acceptable probes. The predefined list can be updated (e.g., by downloading software/firmware updates) as new probes or sensors become available (e.g., obtain governmental approval).

Embodiments of the present invention are directed toward a computer readable medium programmed with instructions that when executed by a processor perform the various steps or algorithms disclosed herein. These algorithms include those disclosed in the figures and related discussion as well as variations thereof.

The circuit-implemented system can include one or more of discrete logic circuitry, programmable logic arrays, specialized processors or general purpose processor programmed specifically programmed. Combinations of these and other circuit elements are also possible and within the scope of various embodiments of the present invention. For example, a system consistent with the aspects shown in FIG. 6 could be implemented in a variety of circuit-based forms, such as through use of data processing circuit modules. More specifically, this is exemplified by a high-speed programmable computer/processor that executes stored instructions to provide operations corresponding to the various blocks of FIG. 6. Alternatively, such a computer/processor could be implemented in combination with discrete and or semi-programmable circuitry, e.g., as Field-Programmable Gate Arrays, Programmable Logic Devices/Arrays). Also various one of the illustrated blocks, and those functions discussed in text, can be implemented using integrated and nonintegrated approaches, e.g., with certain of the blocks located remotely and/or operated disparately relative to the other blocks. Moreover, the methods, devices and systems discussed herein may be implemented in connection with a variety of technologies such as those other than surgery and anatomical settings. The invention may also be implemented using a variety of approaches such as those involving a variety of different sensors and algorithms.

The various embodiments described above are provided by way of illustration only and should not be construed to limit the invention. Based upon the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention, including that set forth in the following claims.

What is claimed is:

1. A circuit-implemented method for use with an actual probe within an anatomical structure, the method comprising:
   for a virtual probe at a virtual location within a model of the anatomical structure, generating virtual image data captured by the virtual probe;
   assessing the virtual image data through a probabilistic comparison of the virtual image data to actual image data captured by the actual probe at an actual location;
   based upon the assessment, updating a correlation between the actual location of the actual probe and a sensed location of the actual probe to provide synchronicity between the sensed location and actual location; and
   for maintaining the synchronicity between a subsequently sensed location and subsequent actual location, using the assessment to select a new virtual location for the virtual probe.

2. The method of claim 1, further including the steps of
   applying weights to a plurality of virtual locations for the virtual probe according to a Bayesian-based probability determination using the assessment of the correlation between the actual location of the actual probe and a sensed location of the actual probe ;
   selecting a subset of virtual locations from the plurality of virtual locations using a uniform distribution across the probability-weighted plurality of virtual locations; and
   assessing virtual image data for the subset of virtual locations to update the weights.

3. The method of claim 1, further including the step of excluding one or more virtual locations from selection based upon a determined probability level for the one or more virtual locations and probability threshold level.

4. The method of claim 1, wherein the model includes a surface mesh model of the anatomical structure.

5. The method of claim 1, wherein the synchronicity is sufficiently maintained to allow real-time tracking of the probe during a surgical procedure.

6. A system comprising:
   a first circuit module to, for a virtual probe at a virtual location within a model of an anatomical structure, generate virtual image data captured by the virtual probe;
   a second circuit module to assess the virtual image data through a probabilistic comparison of the virtual image data to actual image data, the actual image data corresponding to data captured by an actual probe at an actual location;
   a third circuit module to, based upon the assessment, update a correlation between the actual location of the actual probe and a sensed location of the actual probe to provide a measure of synchronicity between the sensed location and actual location; and
   a fourth circuit module to use the assessment to select a new virtual location for the virtual probe for maintaining the synchronicity between a subsequently sensed location and subsequent actual location.

7. The system of claim 6, further including the actual probe that includes an image capture sensor for capturing the actual image data.

8. The system of claim 7, wherein the probe includes a catheter.

9. The system of claim 6, further including a position sensor for determining the sensed location of the probe.

10. The system of claim 9, wherein the position sensor includes an electroanatomic mapping system.

11. A computer-readable nontransitory medium programmed with instructions that when executed by a processor, the processor performs the steps of
    for a virtual probe at a virtual location within a model of the anatomical structure, generating virtual image data captured by the virtual probe;
    assessing the virtual image data through a probabilistic comparison of the virtual image data to actual image data captured by the actual probe at an actual location;
    based upon the assessment, updating a correlation between the actual location of the actual probe and a sensed location of the actual probe to provide synchronicity between the sensed location and actual location; and
    for maintaining the synchronicity between a subsequently sensed location and subsequent actual location, using the assessment to select a new virtual location for the virtual probe.

12. A system for use in connection with an actual probe within an anatomical structure, the system comprising:
    first circuit means for generating, for a virtual probe at a virtual location within a model of the anatomical structure, virtual image data captured by the virtual probe;
    second circuit means for assessing the virtual image data through a probabilistic comparison of the virtual image data to actual image data, the actual image data corresponding to data captured by an actual probe at an actual location;
    third circuit means for updating, based upon the assessment, a correlation between the actual location of the actual probe and a sensed location of the actual probe to provide a measure of synchronicity between the sensed location and actual location; and
    fourth circuit means for using the assessment to select a new virtual location for the virtual probe, for maintaining the synchronicity between a subsequently sensed location and subsequent actual location.

* * * * *